(12) United States Patent
Peterson et al.

(10) Patent No.: US 11,782,521 B2
(45) Date of Patent: Oct. 10, 2023

(54) DISPLAYING APPLICATIONS ON A MOBILE COMPUTING DEVICE BASED ON DIFFERENT RELATIVE POSITIONS

(71) Applicant: Lenovo (United States) Inc., Morrisville, NC (US)

(72) Inventors: Nathan Peterson, Oxford, NC (US); Russell Speight VanBlon, Raleigh, NC (US); Mark Delaney, Raleigh, NC (US); John C. Mese, Cary, NC (US); Arnold Weksler, Raleigh, NC (US)

(73) Assignee: Lenovo (United States) Inc., Morrisville, SC (US)

( * ) Notice: Subject to any disclaimer, the term of this patent is extended or adjusted under 35 U.S.C. 154(b) by 0 days.

(21) Appl. No.: 17/694,555

(22) Filed: Mar. 14, 2022

(65) Prior Publication Data

US 2023/0288993 A1  Sep. 14, 2023

(51) Int. Cl.
| | | |
|---|---|---|
| *G06F 3/03* | (2006.01) | |
| *G06F 3/041* | (2006.01) | |
| *G06F 3/0346* | (2013.01) | |
| *G06F 3/14* | (2006.01) | |

(52) U.S. Cl.
CPC .......... *G06F 3/0346* (2013.01); *G06F 3/0317* (2013.01); *G06F 3/0321* (2013.01); *G06F 3/0412* (2013.01); *G06F 3/14* (2013.01)

(58) Field of Classification Search
CPC .... G06F 3/0346; G06F 3/0317; G06F 3/0321; G06F 3/0412; G06F 3/042; G06F 3/044; G06F 3/14
See application file for complete search history.

(56) References Cited

U.S. PATENT DOCUMENTS

| | | | | |
|---|---|---|---|---|
| 7,676,332 | B2 * | 3/2010 | Damen | A61B 5/222 |
| | | | | 702/182 |
| 9,538,251 | B2 * | 1/2017 | Aravamudan | H04N 21/812 |
| 9,734,304 | B2 * | 8/2017 | Blackadar | A61B 5/1123 |
| 11,497,980 | B2 * | 11/2022 | Putnam | G06Q 50/01 |
| 2015/0382071 | A1 * | 12/2015 | Aravamudan | H04N 21/812 |
| | | | | 725/14 |

* cited by examiner

*Primary Examiner* — Nvijay Shankar
(74) *Attorney, Agent, or Firm* — Kunzler Bean & Adamson

(57) ABSTRACT

Methods, apparatus, and computer program products that can display applications on a mobile computing device based on different relative positions are disclosed herein. One method includes determining, by a processor, different relative positions of a mobile computing device user while a user is performing an activity. In some embodiments, the method further includes toggling display of a plurality of applications on the mobile computing device based on the different relative positions of the mobile computing device while the user is performing the activity. Apparatus and computer program products that include hardware and/or software that can perform the methods for display applications on a mobile computing device based on position are also disclosed herein.

20 Claims, 10 Drawing Sheets

DISPLAYING APPLICATIONS ON A MOBILE COMPUTING DEVICE BASED ON DIFFERENT RELATIVE POSITIONS

FIELD

The subject matter disclosed herein relates to computing devices and more particularly relates to displaying applications on a mobile computing device based on different relative positions.

BACKGROUND

When users of a mobile computing device are engaged in some activities, it is sometimes difficult to interact with their mobile computing device to change between applications. For example, some joggers may want to listen to music, check their running distance, and check their biometrics (e.g., heartrate, etc.) while jogging. Conventional mobile computing devices typically require users to in some manner use their finger to interact with applications on their respective mobile computing devices while engaging in activities, which is less user-friendly than they otherwise could be.

BRIEF SUMMARY

Apparatus, methods, and program products that can display applications on a mobile computing device based on different relative positions are disclosed herein. An apparatus, in one embodiment, includes a processor and a memory that stores code executable by the processor. In certain embodiments, the code is executable by the processor to determine different relative positions of a mobile computing device while a user is performing an activity and toggle display of a plurality of applications on the mobile computing device based on the different relative positions of the mobile computing device while the user is performing the activity.

One embodiment of a method that can display applications on a mobile computing device based on different relative positions includes determining, by a processor, different relative positions of a mobile computing device user while a user is performing an activity. In some embodiments, the method further includes toggling display of a plurality of applications on the mobile computing device based on the different relative positions of the mobile computing device while the user is performing the activity.

A computer program product that can display applications on a mobile computing device based on different relative positions, in one embodiment, includes a computer-readable storage medium including program instructions embodied therewith. In certain embodiments, the program instructions are executable by a processor to cause the processor to determine different relative positions of a mobile computing device while the user is performing an activity and toggle display of a plurality of applications on the mobile computing device based on the different relative positions of the mobile computing device while the user is performing the activity.

BRIEF DESCRIPTION OF THE DRAWINGS

A more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which.

DETAILED DESCRIPTION

Figure 1A:
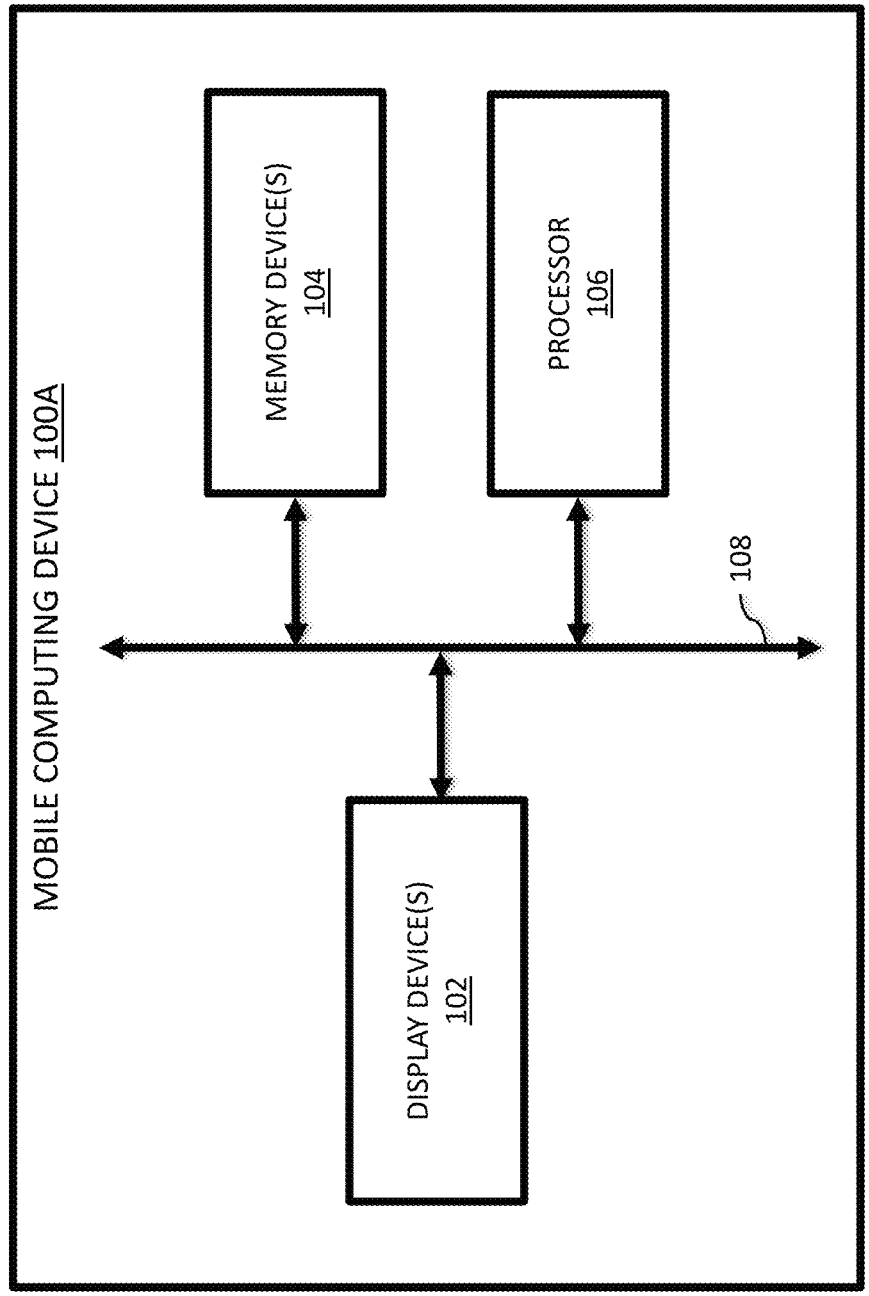
FIGS. 1A and 1B are schematic block diagrams illustrating various embodiments of mobile computing device that can display applications on a mobile computing device based on different relative positions of the mobile computing device.

As will be appreciated by one skilled in the art, aspects of the embodiments may be embodied as a system, method, or program product. Accordingly, embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments may take the form of a program product embodied in one or more computer readable storage devices storing machine readable code, computer readable code, and/or program code, referred hereafter as code. The storage devices may be tangible, non-transitory, and/or non-transmission. The storage devices may not embody signals. In a certain embodiment, the storage devices only employ signals for accessing code.

Many of the functional units described in this specification have been labeled as modules, in order to emphasize their implementation independence more particularly. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in code and/or software for execution by various types of processors. An identified module of code may, for instance, comprise one or more physical or logical blocks of executable code which may, for instance, be organized as an object, procedure, or function. Nevertheless, the executables of an identified module need not be physically located together but may comprise disparate instructions stored in different locations which, when joined logically together, comprise the module and achieve the stated purpose for the module.

Indeed, a module of code may be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different computer readable storage devices. Where a module or portions of a module are implemented in software, the software portions are stored on one or more computer readable storage devices.

Any combination of one or more computer readable medium may be utilized. The computer readable medium may be a computer readable storage medium. The computer readable storage medium may be a storage device storing the code. The storage device may be, for example, but not limited to, an electronic, magnetic, optical, electromagnetic, infrared, holographic, micromechanical, or semiconductor system, apparatus, or device, or any suitable combination of the foregoing.

More specific examples (a non-exhaustive list) of the storage device would include the following: an electrical connection having one or more wires, a portable computer diskette, a hard disk, a random-access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Code for carrying out operations for embodiments may be written in any combination of one or more programming languages including an object-oriented programming language such as Python, Ruby, Java, Smalltalk, C++, or the like, and conventional procedural programming languages, such as the "C" programming language, or the like, and/or machine languages such as assembly languages. The code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to," unless expressly specified otherwise. An enumerated listing of items does not imply that any or all of the items are mutually exclusive, unless expressly specified otherwise. The terms "a," "an," and "the" also refer to "one or more" unless expressly specified otherwise.

In addition, as used herein, the term, "set," can mean one or more, unless expressly specified otherwise. The term, "sets," can mean multiples of or a plurality of one or mores, ones or more, and/or ones or mores consistent with set theory, unless expressly specified otherwise.

Furthermore, the described features, structures, or characteristics of the embodiments may be combined in any suitable manner. In the following description, numerous specific details are provided, such as examples of programming, software modules, user selections, network transactions, database queries, database structures, hardware modules, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

Aspects of the embodiments are described below with reference to schematic flowchart diagrams and/or schematic block diagrams of methods, apparatuses, systems, and program products according to embodiments. It will be understood that each block of the schematic flowchart diagrams and/or schematic block diagrams, and combinations of blocks in the schematic flowchart diagrams and/or schematic block diagrams, can be implemented by code. This code may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The code may also be stored in a storage device that can direct a computer, other programmable data processing apparatus, or other devices to function in a particular manner, such that the instructions stored in the storage device produce an article of manufacture including instructions which implement the function/act specified in the schematic flowchart diagrams and/or schematic block diagrams block or blocks.

The code may also be loaded onto a computer, other programmable data processing apparatus, or other devices to cause a series of operational steps to be performed on the computer, other programmable apparatus, or other devices to produce a computer implemented process such that the code which execute on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods, and program products according to various embodiments. In this regard, each block in the schematic flowchart diagrams and/or schematic block diagrams may represent a module, segment, or portion of code, which comprises one or more executable instructions of the code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

The description of elements in each figure may refer to elements of proceeding figures. Like numbers refer to like elements in all figures, including alternate embodiments of like elements.

Apparatus, methods, and program products that can display applications on a mobile computing device based on different relative positions are disclosed herein. An apparatus, in one embodiment, includes a processor and a memory that stores code executable by the processor. In certain embodiments, the code is executable by the processor to determine different relative positions of a mobile computing device while a user is performing an activity and toggle display of a plurality of applications on the mobile computing device based on the different relative positions of the mobile computing device while the user is performing the activity.

One embodiment of a method that can display applications on a mobile computing device based on different relative positions includes determining, by a processor, different relative positions of a mobile computing device user while a user is performing an activity. In some embodiments, the method further includes toggling display of a plurality of applications on the mobile computing device based on the different relative positions of the mobile computing device while the user is performing the activity.

A computer program product that can display applications on a mobile computing device based on different relative positions, in one embodiment, includes a computer-readable storage medium including program instructions embodied therewith. In certain embodiments, the program instructions are executable by a processor to cause the processor to determine different relative positions of a mobile computing device while the user is performing an activity and toggle display of a plurality of applications on the mobile computing device based on the different relative positions of the mobile computing device while the user is performing the activity.

Figure 1B:
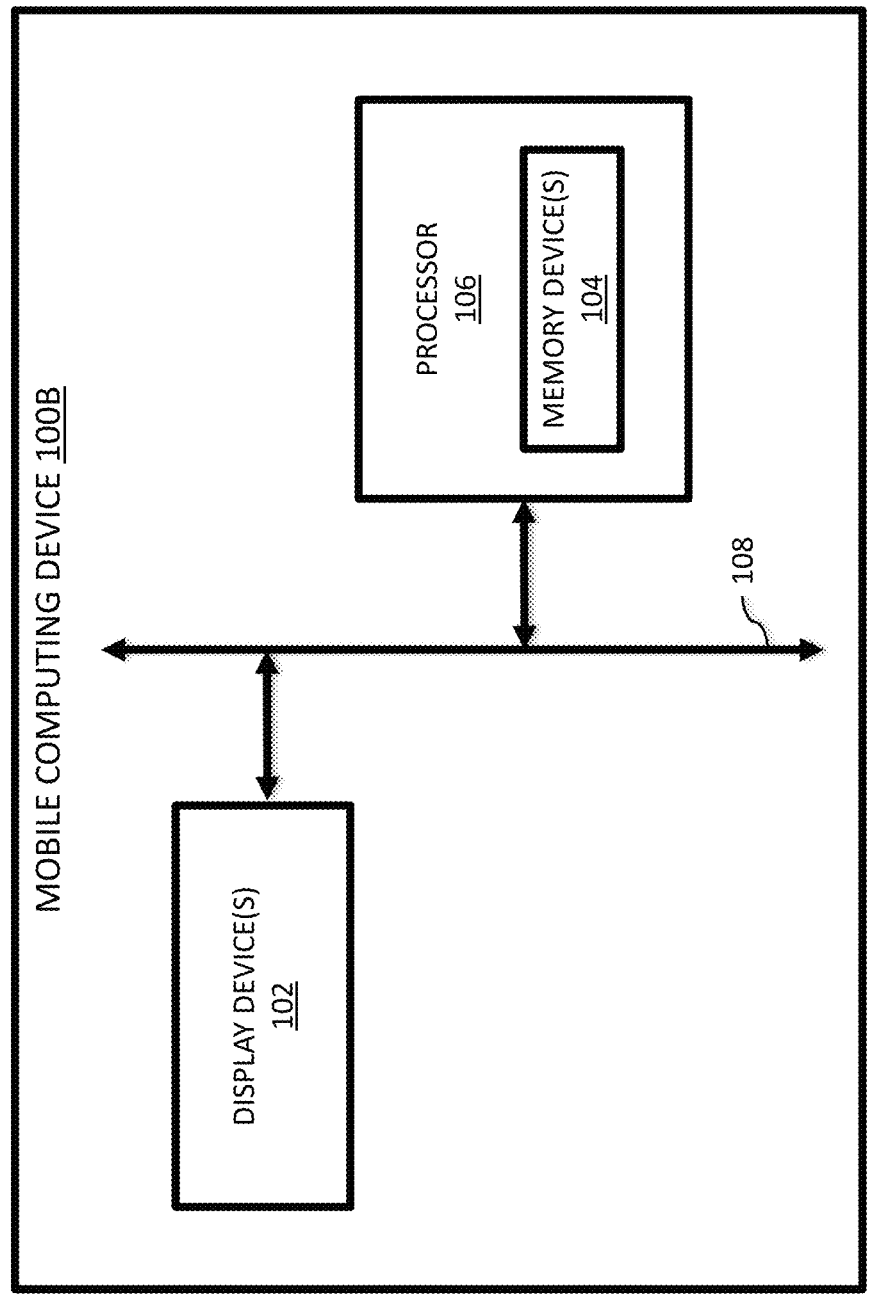

Turning now to the drawings, FIGS. 1A and 1B are block diagram of various embodiments of a mobile computing device 100A and a mobile computing device 100B, respectively. Specifically, the mobile computing devices 100A and 100B illustrated in FIGS. 1A and 1B are configured to respectively display applications based on different relative positions of the mobile computing device 100A and the mobile computing device 100B. As discussed herein, the mobile computing devices 100A and 100B may simply be referred to individually or collectively as, mobile computing device(s) 100.

A mobile computing device 100 (e.g., mobile computing devices 100A and 100B) may include any suitable mobile computing device/system that is known or developed in the future, which can also be referred to herein generally as, a mobile information handling device. Examples of a mobile computing device 100 include, but are not limited to, a wearable device (e.g., a smart watch, a smart ring, a fitness tracker, etc.), a smart phone, a cellular telephone, a laptop computer, a computing tablet, and a personal digital assistant (PDA), etc., among other computing devices that are mobile that are possible and contemplated herein.

At least in the embodiment illustrated in FIG. 1A, a mobile computing device 100A includes, among other components, one or more display devices 102 (or display(s) 102), a set of memory devices 104 (or memory 104), and at least one processor 106A coupled to and/or in communication with one another via a bus 108 (e.g., a wired and/or wireless bus). At least in the embodiment illustrated in FIG. 1B, a mobile computing device 100B includes, among other components, one or more display devices 102, a set of memory devices 104, and at least one processor 106B coupled to and/or in communication with one another via a bus 108. Alternative to the processor 106A in the mobile computing device 100A, the processor 106B in the mobile computing device 100B includes the memory device(s) 104 in the processor 106B, whereas the memory device(s) 104 of the computing device 100A is/are separate and/or independent of the processor 106A. As discussed herein, the processors 106A and 106B may simply be referred to individually or collectively as, processor(s) 106.

As illustrated in FIGS. 1A and 1B, a display device 102 may include any suitable device and/or system that is known or developed in the future capable of displaying a set of applications, a set of images, a set of video feeds, and/or a set of video streams, etc. In various embodiments, the display device 102 includes an internal and/or built-in display.

The display device 102, in various embodiments, is configured to toggle the display of a plurality of applications in response to receiving commands from a processor 106 to do such, as discussed elsewhere herein. That is, the display device 102 is configured to switch between displaying two or more applications in response to receiving commands and/or signals from a processor 106 to do such, as discussed elsewhere herein.

A set of memory devices 104 may include any suitable quantity of memory devices 104. Further, a memory device 104 may include any suitable type of device and/or system that is known or developed in the future that can store computer-useable and/or computer-readable code. In various embodiments, a memory device 104 may include one or more non-transitory computer-usable mediums (e.g., readable, writable, etc.), which may include any non-transitory and/or persistent apparatus or device that can contain, store, communicate, propagate, and/or transport applications, instructions, data, computer programs, software, code, routines, etc., for processing by or in connection with a computer processing device (e.g., processor 106A and/or processor 106B).

A memory device 104, in some embodiments, includes volatile computer storage media. For example, a memory device 104 may include random access memory (RAM), including dynamic RAM (DRAM), synchronous dynamic RAM (SDRAM), and/or static RAM (SRAM). In other embodiments, a memory device 104 includes non-volatile computer storage media. For example, a memory device 104 may include flash memory and/or any other suitable non-volatile computer storage device that is known or developed in the future. In various embodiments, a memory device 104 includes both volatile and non-volatile computer storage media.

Figure 2A:
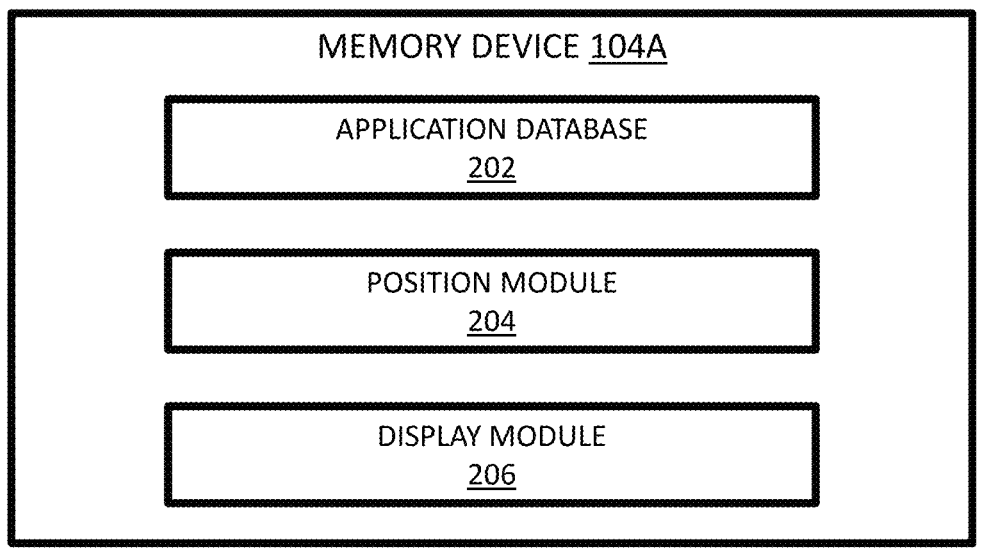
FIGS. 2A and 2B are schematic block diagrams illustrating various embodiments of a memory device included in the mobile computing devices of FIGS. 1A and 1B.

With reference now to FIG. 2A, FIG. 2A is a schematic block diagram of one embodiment of a memory device 104. At least in the illustrated embodiment, the memory device 104 includes, among other components, an application database 202, a position module 204, and a display module 206 that are each configured to operate/function in conjunction with one another when executed by a processor 106 to display applications based on the relative position of a mobile computing device 100.

An application database 202 may include any suitable hardware and/or software capable of storing, organizing, and/or managing a plurality of applications that can executed by a processor 106 for display on a display device 102. A plurality of applications may include any suitable quantity of applications greater than or equal to two (2) applications.

In certain embodiments, a plurality of applications includes two (2) applications. In additional or alternative embodiments, a plurality of applications includes three (3) applications. In further additional or alternative embodiments, a plurality of applications includes four (4) applications. In still further additional or alternative embodiments, a plurality of applications includes five (5) or more applications, which maximum quantity may be any suitable quantity of applications capable of being stored on and executed by a mobile computing device 100.

The type(s) and/or category/categories of the applications stored on, organized by, and/or managed by the application database 202 may include any suitable type and/or category of application that is/are known or developed in the future. Example types/categories of applications (apps) include, but are not limited to, educational applications (e.g., learning applications, weather applications, news applications, books, etc.), lifestyle applications (e.g., fitness applications, biometric applications, food/drink applications, camera/video applications, etc.), social media applications, productivity applications (e.g., email, voicemail, dictation, video/voice conferencing, etc.), entertainment applications (e.g., music applications, streaming applications, podcasts, books, etc.), gaming applications, and/or navigation applications (e.g., global positioning system (GPS) applications, maps, etc.), etc., among other types/categories of applications that are possible and contemplated herein. Further, the application(s) stored on, organized by, and/or managed by the application database 202 may include any suitable application and/or applications that is/are known or developed in the future including one or more particular applications and/or one or more specific applications.

A position module 204 may include any suitable hardware and/or software that can determine the position(s) of a mobile computing device 100 relative to an object and/or a feature of the object. In other words, the position module 204 is configured to determine the relative position(s) of the mobile computing device 100 with respect to an object and/or feature of the object, which can include any suitable object and/or feature of an object that is known or developed in the future.

In certain embodiments, the object includes a user of the mobile computing device 100 or an item associated with the user (e.g., an item of personal property, a vehicle, a building, etc.), among other objects that are possible and contemplated herein. The feature of the user my include any suitable feature (e.g., body part) of the user or any suitable feature of the object associated with the user. Example features of a user include, but are not limited, the user's head, hair, eyes, ears, nose, mouth, chin, shoulders, arms, front torso, back, waist, arms, legs, and feet, etc., among other features of a user that are possible and contemplated herein.

The relative position(s) of a mobile computing device 100 may be determined and/or detected using any suitable hardware and/or software that is known or developed in the future. For example, the relative position(s) of the mobile computing device 100 may be determined using a gyroscope, a camera, a microphone, and/or a thermal detection device, etc., among other devices that are capable of determining/detecting the relative positions of at least two objects (e.g., a user and a mobile computing device 100) that are possible and contemplated herein.

The relative position(s) may include any suitable position and/or positions relative to two or more objects and/or the feature(s) of one or more objects. For example, a relative position may be a height above an object and/or feature of an object, a height at or equal to an object and/or feature of an object, a height below an object and/or feature of an object, a position to the left of an object and/or feature of an object, a position at or equal to an object and/or feature of an object, a position to the right of an object and/or feature of an object, a distance less than a predetermined distance from an object and/or feature of an object, a distance at a predetermined distance from an object and/or feature of an object, a distance greater than a predetermined distance from an object and/or feature of an object, and/or combinations thereof, etc., among other relative positions that are possible and contemplated herein. In another non-limiting example, a first relative position may be with respect to a first object and/or feature of the first object and a second relative position may be with respect to a second object and/or feature of the second object. As such, the various embodiments provide that the relative positions may be with respect to the same object, with respect to different objects, with respect to the same feature on the same object, with respect to different features on the same object, with respect to the same feature on different objects, and with respect to different features on different objects.

In various embodiments, the position module 204 is configured to transmit a message and/or signal to the display module 206 each time the position module 204 determines and/or detects that a mobile computing device 100A/100B is in moved to a new and/or different relative position. That is, the position module 204 is configured to transmit the message and/or signal to the display module 206 each time the position module 204 determines and/or detects that a mobile computing device 100 is in relative position with respect to and/or reference to an object and/or a feature of an object (e.g., a position relative to a reference object and/or a reference feature of a reference object), which can include a new relative position and/or a different relative position.

In various embodiments, the message and/or signal generated by the position module 206 includes an indication of and/or identifies the position of the mobile computing device 100 relative to the reference object and/or reference feature. That is, the message and/or signal can notify the display module 206 of the relative position of the mobile computing device 100.

Various embodiments of a display module 206 are configured to receive the messages and/or signals from the position module 204 notifying the display module 206 of the relative position of the mobile computing device 100 and/or identifying the relative position of the mobile computing device 100. In addition, a display module 206 may further include any suitable hardware and/or software that can display and/or facilitate display of applications on one or more display devices 102.

In various embodiments, the display module 206 is configured to toggle displaying multiple applications and/or toggle displaying a plurality of applications on the one or more display devices 102 of a mobile computing device 100. That is, the display module 206 is configured to switch between displaying two or more applications on the display device(s) 102 responsive to the different relative positions of the mobile computing device 100.

In some embodiments, the display module 206 is configured to switch/toggle between displaying two applications on the display device(s) 102 responsive to the mobile computing device 100 being located at two different relative positions with respect to and/or reference to a reference object and/or reference feature of a reference object. In other embodiments, the display module 206 is configured to switch/toggle between displaying three applications on the display device(s) 102 responsive to the mobile computing device 100 being located at three different relative positions with respect to and/or reference to a reference object and/or reference feature of a reference object. In still other embodiments, the display module 206 is configured to switch/toggle between displaying four applications on the display device(s) 102 responsive to the mobile computing device 100 being located at two different relative positions with respect to and/or reference to a reference object and/or reference feature of a reference object. In further embodiments, the display module 206 is configured to switch/toggle between displaying five or more applications on the display device(s) 102 responsive to the mobile computing device 100 being located at a corresponding five or more different relative positions with respect to and/or reference to a reference object and/or reference feature of a reference object.

The display module 206, in various embodiments, is configured to toggle and/or switch between displaying various applications on the display device(s) 102 based on the relative position of the mobile computing device 100. That is, the display module 206 is configured to display different applications on the display device(s) 102 based on the different relative positions at which the mobile computing device 100 may be positioned.

For example, the display module 206 may be configured to display and/or facilitate displaying a first application on the display device(s) 102 in response to receiving a message/signal from the position module 204 indicating that a mobile computing device 100 is positioned/located at a first relative location and display and/or facilitate displaying a second (different) application on the display device(s) 102 in response to receiving a message/signal from the position module 204 indicating that the mobile computing device 100 is positioned/located at a second (different) relative position. Further, the display module 206 can again display and/or facilitate displaying the first application on the display device(s) 102 in response to receiving a further message/signal from the position module 204 indicating that the mobile computing device 100 is again positioned/located at the first relative location and again display and/or facilitate displaying the second application on the display device(s) 102 in response to receiving a second further message/signal from the position module 204 indicating that the mobile computing device 100 is again positioned/located at the second relative location. This process can be repeated each time that the mobile computing device 100 is determined/detected as being positioned/located at the first relative location and the second relative location and the display module 206 receives a message/signal from the position module 204 indicating such. It is in this manner that the display module 206 is configured to display and/or facilitate displaying a particular application on the display device 102 of a mobile computing device 100 when the mobile computing device 100 is located/positioned at a particular relative location and/or toggle/switch between displaying and/or facilitating the display of different applications on the display device(s) 102 of a mobile computing device 100 based on the mobile computing device 100 being positioned/located at different relative positions with respect to an object (e.g., a reference object) and/or a feature (e.g., a reference feature) of an object/reference object.

Notably, the above non-limiting example is provided so that various embodiments and/or aspects of the various embodiments can be more readily understood and is not intended to limit the spirit and/or scope of the various embodiments and/or aspects in any manner. That is, various other embodiments may toggle/switch between a quantity of applications greater than two applications in response to the mobile computing device 100 as being positioned/located at a corresponding greater quantity of relative positions with respect to an object and/or a feature of an object.

In various embodiments, the display module 206 is configured to assign the different applications to the different relative locations so that the correct application is properly displayed on the display device(s) 102 when the mobile computing device 100 is positioned/located at a corresponding/associated relative location. In some embodiments, the user assigns an application to a corresponding relative location. That is, the user can assign a first application to a first relative location so that the first application is displayed on the display device(s) 102 when the mobile computing device 100 is positioned/located at the first relative location and assign a second application to a second relative location so that the second application is displayed on the display device(s) 102 when the mobile computing device 100 is positioned/located at the second relative location, and so forth. For example, a user may assign a music application to the user's waist (e.g., a first relative location) so that the display device(s) 102 display the music application when the mobile computing device 100 is positioned/located at the user's waist and assign a video streaming application to an eye level of the user (e.g., a second relative location) so that the display device(s) 102 display the video streaming application when the mobile computing device 100 is positioned/located at the eye level of the user.

In other embodiments, the display module 206 is configured to automatically and/or automatedly assign the applications to the relative positions. In some embodiments, the display module 206 is configured to randomly assign the applications to respective relative positions. That is, the display module 206 may randomly assign a first application to a first relative position and randomly assign a second application to a second (different) relative position and so forth for each additional application/relative position combination.

In other embodiments, the display module 206 is configured to automatically and/or automatedly assign applications to respective relative positions based on a nexus of the historical use of each application and the relative position at which the user historically views/uses each application. That is, the display module 206 may, based on tracking application use and the position(s) at which an application is used over time, automatically and/or automatedly assign a first application to a first relative position in response to the user historically viewing/using the first application while the mobile computing device 100 is located/positioned at the first relative location and, further based on tracking the application use and position(s) of use, automatically and/or automatedly assign a second application to a second (different) relative position in response to the user historically viewing/using the second application while the mobile computing device 100 is located/positioned at the second relative location, and so forth for each additional application/relative position combination. With reference again to the above example, the user may historically use the music application while the mobile computing device 100 is positioned at the user's waist and historically use/view the video streaming application while the mobile computing device 100 is positioned at the user's eye level and, in response to tracking such, the display module 206 can automatically and/or automatedly assign the music application to the user's waist and automatically and/or automatedly assign the video streaming application to the user's eye level such that the music application is displayed on the display device(s) 102 when the mobile computing device 100 is located/positioned at the user's waist and the video streaming application is displayed on the display device(s) 102 when the mobile computing device 100 is located/positioned at the eye level of the user.

Figure 2B:
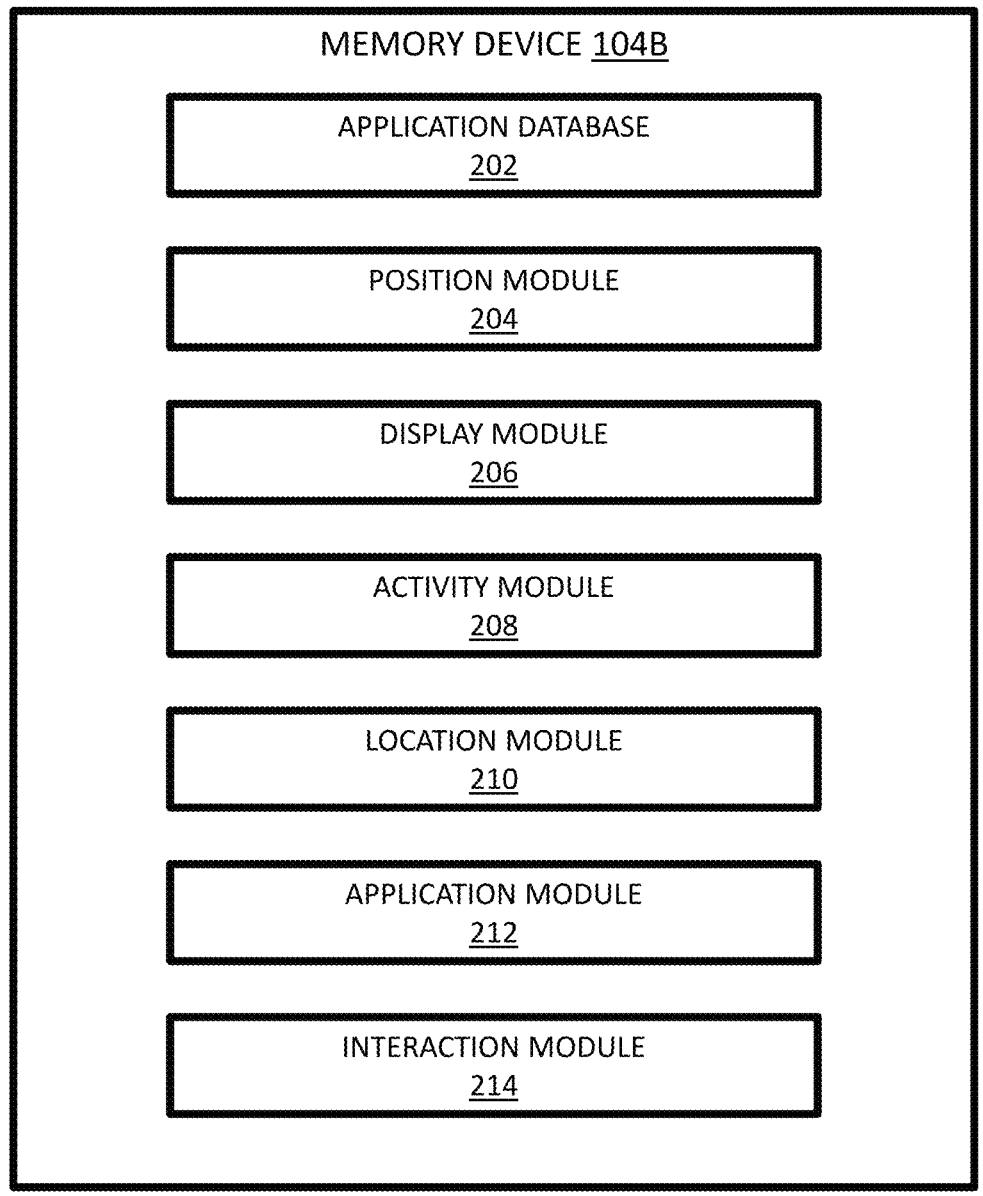

Referring now to FIG. 2B, FIG. 2B is a block diagram of another embodiment of a memory device 104B. The memory device 104B includes an application database 202, a position module 204, and a display module 206 similar to the application database 202, position module 204, and display module 206 included in the memory device 104A discussed with reference to FIG. 2A. At least in the embodiment illustrated in FIG. 2B, the memory device 104B further includes, among other components, an activity module 208, a location module 210, an application module 212, and an interaction module 214.

An activity module 208 may include any suitable hardware and/or software that can determine an activity that a user is currently performing. In various embodiments, the activity module 208 is configured to monitor the movements and/or speech of a user and determine the type of activity and/or specific activity that the user is currently performing based on the monitored movements and/or speech for the user.

The determined type of activity may be any suitable type of activity that is known or developed in the future that a user is capable of performing and may desire using/viewing multiple applications on a mobile computing device 100 while the user is performing the type of activity. Example types of activity may include, but are not limited to, exercise, sports, work/employment, educational/school, leisure activities, religious activities/ceremonies, transportation, security activities, social activities, and culinary activities, etc., among other types of activities that are possible and contemplated herein.

While particular types of activities are discussed herein, the particular types of activities are for illustrative purposes and are not intended to limit the scope of the spirit and scope of the various embodiments in any manner. As such, various other embodiments may include any other suitable type(s) of activity that are possible, each of which is contemplated herein.

In addition, the determined specific activity may be any suitable activity that is known or developed in the future that a user is capable of performing and may desire using/viewing multiple applications on a mobile computing device 100 while the user is performing the activity. Example specific activities may include, but are not limited to, jogging, running, walking, cycling, boating, cooking, golfing, studying, and working, etc., among other specific activities that are possible and contemplated herein.

While specific activities are discussed herein, the specific activities are for illustrative purposes and are not intended to limit the scope of the spirit and scope of the various embodiments in any manner. As such, various other embodiments may include any other suitable activity and/or activities that are possible, each of which is contemplated herein.

The activity module 208, in various embodiments, is configured to transmit a signal and/or message to the application module 212 in response to determining/detecting which type of activity and/or what activity the user is currently performing. The signal and/or message can notify, identify, and/or inform the application module 212 which type of activity and/or what specific activity the user is currently performing.

A location module 210 may include any suitable hardware and/or software that can determine the location of a user. In various embodiments, the location module 210 is configured to monitor the movements of a user and determine the current geographic location of the user based on the monitored movements.

The determined geographic location may include any suitable geographic location that is known or developed in the future where a user can be present. A geographic location may include a relatively large/general geographic area/location and/or a relatively small/specific geographic area/location. Example relatively large/general geographic areas/locations can include, but are not limited to, a continent, a geographic region, a country, a state, a city/town, etc., among other relatively large/general geographic areas/locations that are possible and contemplated herein. Example relatively small/specific geographic areas/locations can include, but are not limited to, a town/city district, a landmark, a street, a building, and a room, etc., among other relatively small/specific geographic areas/locations that are possible and contemplated herein.

The location module 210, in various embodiments, is configured to transmit a signal and/or message to the application module 212 in response to determining/detecting the user's current geographic location. The signal and/or message can notify, identify, and/or inform the application module 212 the geographic location where the user is currently present.

In some embodiments, an application module 212 is configured to receive the messages and/or signals from the activity module 208 that notify, identify, and/or inform the application module 212 which type of activity and/or what specific activity the user is currently performing and/or the messages. In addition, an application module 212 may include any suitable hardware and/or software that can assign applications in the application database 202 to various types of activities and/or various specific activities for use and/or viewing by the user while the user is performing a particular type of activity and/or specific activity.

Applications may be assigned to a particular type of activity and/or to a specific activity based on any suitable criteria/criterion that is known or developed in the future. In various embodiments, a user assigns the applications to the particular types of activity and/or to the specific activities and the application module 212 is configured to implement the user's assignment(s). For example, a user can assign a music application, a navigation application (e.g., GPS), and/or a biometric application, among other application possibilities, to cycling (exercise/sport), among other possible types of activities and/or possible activities, because the user desires the ability to listen to music while cycling, desires the ability to obtain directions and/or follow a route while cycling, and/or desires the ability to check/monitor the user's heartrate while cycling, respectively.

In additional or alternative embodiments, the application module 212 automatically and/or automatedly assigns and implements the applications to the particular types of activity and/or to the specific activities. In some embodiments, the application module 212 randomly assigns and implements the applications to the particular types of activity and/or to the specific activities. In other embodiments, the application module 212 automatically and/or automatedly assigns and implements the applications to the particular types of activity and/or to the specific activities based on a historical nexus of the historical use of each application and the particular type of activity and/or specific activity that the user is performing when viewing/using each application. That is, the application module 212 may, based on tracking application use and the particular type of activity and/or specific activity that the user is performing when using/viewing an application over time, automatically and/or automatedly assign a first application to a first particular type of activity and/or first specific activity in response to the user historically viewing/using the first application while the user is performing the first particular type of activity and/or first specific activity and, further based on tracking the application use and the particular type of activity and/or specific activity, automatically and/or automatedly assign a second application to a second (different) particular type of activity and/or second (different) specific activity in response to the user historically viewing/using the second application while performing the second particular type of activity and/or second specific activity, and so forth for each additional application/type of activity and/or application/activity combination.

In further additional or alternative embodiments, the application module 212 is configured to receive the messages and/or signals from the location module 210 that notify, identify, and/or inform the application module 212 the geographic location where the user is currently present. Here, the application module 212 may include any suitable hardware and/or software that can assign applications in the application database 202 to various geographic locations for use and/or viewing by the user while the user is present at the geographic locations.

Applications may be assigned to a particular geographic location based on any suitable criteria/criterion that is known or developed in the future. In various embodiments, a user assigns the applications to the particular geographic locations and the application module 212 is configured to implement the user's assignment(s). For example, a user can assign a navigation application (e.g., GPS) to a particular country, state, city/town, etc., a video conferencing application to an employer's building, office, etc. and/or a gaming application to a bedroom, game room, etc., among other application and/or geographic location possibilities that are possible and contemplated herein.

In additional or alternative embodiments, the application module 212 automatically and/or automatedly assigns and implements the applications to the particular geographic locations. In some embodiments, the application module 212 randomly assigns and implements the applications to the geographic locations. In other embodiments, the application module 212 automatically and/or automatedly assigns and implements the applications to the particular geographic locations based on a historical nexus of the historical use of each application and the particular geographic location where the user typically and/or most often views/uses each application. That is, the application module 212 may, based on tracking application use and the particular the particular geographic location where the user typically and/or most often views/uses each application over time, automatically and/or automatedly assign a first application to a first geographic location in response to the user historically viewing/using the first application while the user is present at the first geographic location and, further based on tracking the application use and the particular geographic location, automatically and/or automatedly assign a second application to a second (different) particular geographic location in response to the user historically viewing/using the second application while present at the second particular geographic location, and so forth for each additional application/geographic location combination.

An interaction module 214 may include any suitable hardware and/or software that can perform one or more operations and/or functions of an application currently being displayed on the display device(s) 102 of a mobile computing device 100. In various embodiments, the interaction module 214 is configured to perform the operation(s) and/or function(s) of the application currently being displayed on the display device(s) 102 of the mobile computing device 100 in response to receiving one or more inputs (e.g., interactive inputs) from the user while the application is being displayed on the display device(s) 102.

The operation(s) and/or function(s) performed by the interactive module 214 may include any suitable operation(s) and/or function(s) that are known or developed in the future included within an application currently being displayed on the display device(s) 102. Further, the input(s) may include any suitable input that is known or developed in the future.

In some embodiments, the inputs from the user can be received via the user using a touch input (e.g., a touch screen input and/or a button input) and/or using an auditory input (e.g., a voice command). In alternative embodiments, the inputs from the user can be received without the user using a touch input and/or using an auditory input.

In certain embodiments, the user input(s) is/are received from the user via the user viewing the application in different view modes (e.g., landscape, portrait, etc.). That is, the display module 206 can switch between application based on whether a mobile computing device 100 is being held in a landscape position and/or portrait position, as detected/determined by the interactive module 214. For example, some games/gaming applications will not work in portrait mode, thus if the user starts to hold the mobile computing device 100 in portrait, a game/gaming application becomes inoperable. Accordingly, in response to the interactive module 214 detecting/determining that the user has switched from a landscape mode to a portrait hold on the mobile computing device 100, the display device 206 in configured to switch back to displaying and/or facilitating display of a home screen, an email application, or another suitable application. In addition, in response to the interactive module 214 detecting/determining that the user has switched from the portrait mode back to the landscape hold on the mobile computing device 100, the display device 206 in configured to switch back to displaying and/or facilitating display of the game/gaming application.

In additional or alternative embodiments, the user input(s) is/are received from the user via the user changing an orientation of the mobile computing device 100 (e.g., tilting, angling, etc.), moving the mobile device 100 in a predefined pattern (e.g., in a circle, up/down, right/left, etc.), and/or shaking the mobile computing device 100, etc., while the display device(s) 102 are displaying the application and the mobile computing device 100 is located/positioned at a particular relative position, among other types of inputs and/or particular inputs that are possible and contemplated herein. For example, while the mobile computing device 100 is located/positioned at a user's waist (e.g., a predefined relative position) and is currently displaying a music application that is assigned for display while the mobile computing device 100 is located/positioned at the user's waist, the user can provide a first input to the interactive module 214 to skip the current song by tilting a display device 102 (e.g., a display screen) of the mobile computing device 100 away from the user and provide a second input to the interactive module 214 to repeat the current song by tilting the display device 102 of the mobile computing device 100 toward the user, among other examples of applications and/or inputs that are possible and contemplated herein.

In various embodiments, different applications can include the same type of input, the same inputs, different types of user input, and/or different user inputs to perform the function(s)/operation(s) of the various applications in the application database 202. As such, the interactive module 214 is configured to associate the various inputs and/or input types with the various different applications such that the interactive module 214 can perform the various operation(s) and/or function(s) of the applications responsive to receiving the same or different user inputs and/or input types while the applications are being displayed on the display device(s) 102 while the mobile computing device 100 is located/positioned at the corresponding relative position assigned to each application.

The following non-limiting is a continuation of the immediately above example in which the music application is displayed at the user's waist and the user can provide tile inputs to skip and repeat songs. In this non-limiting example, after the user moves the mobile computing device from the user's waist to the user's chest/torso (e.g., the user changes the relative position of the mobile computing device 100 and/or the mobile computing device 100 is now located/positioned at a new/different relative position) and a biometric application that is assigned for display while the mobile computing device 100 is located/positioned at the user's chest/torso is currently being displayed on the display device(s) 102, the user can make the same user inputs (e.g., tilt the display device 102) or different user inputs (e.g., shake the mobile computing device 100 and/or move the mobile computing device 100 in one or more predefined patterns, etc.) to change (e.g., scroll) between displaying the user's heartrate and displaying an oxygen level, respiration rate, and/or other suitable biometric data for the user responsive to the interactive module 214 receiving the various user inputs to the biometric application while the biometric application is being displayed on the display device(s) 102 responsive to the mobile computing device 100 being currently located/positioned at the user's chest/torso, among other applications and/or operation(s)/function(s) that are possible and contemplated herein.

In certain embodiments, the interactive module 214 can identify, detect, and/or determine when an application needs a touch input from the user and the user is unable to provide the touch input (e.g., the user cannot reach the mobile computing device 100 and/or both of the user's hands are full, etc.). Here, the interactive module 214 is configured to enable the user to utilize user inputs to toggle, switch, and/or scroll through the currently selected applications regardless of the current relative position of the mobile computing device 100. In other words, the interactive module 214 is configured to default to and/or override the relative position-application display functionality and enable the user to utilize user inputs as a technique for toggling, switching, and/or scrolling through the currently selected applications when the user is unable to provide touch inputs needed by the mobile computing device 100.

Referring back to FIGS. 1A and 1B, a processor 106 may include any suitable non-volatile/persistent hardware and/or software configured to perform and/or facilitate performing functions and/or operations for displaying applications on a mobile computing device 100 based on different relative positions. In various embodiments, the processor 106 includes hardware and/or software for executing instructions in one or more modules and/or applications that can perform and/or facilitate performing functions and/or operations for displaying applications on a mobile computing device based on different relative positions. The modules and/or applications executed by the processor 106 for displaying applications on a mobile computing device based on different relative positions can be stored on and executed from a memory device 104 and/or from the processor 106.

Figure 3A:
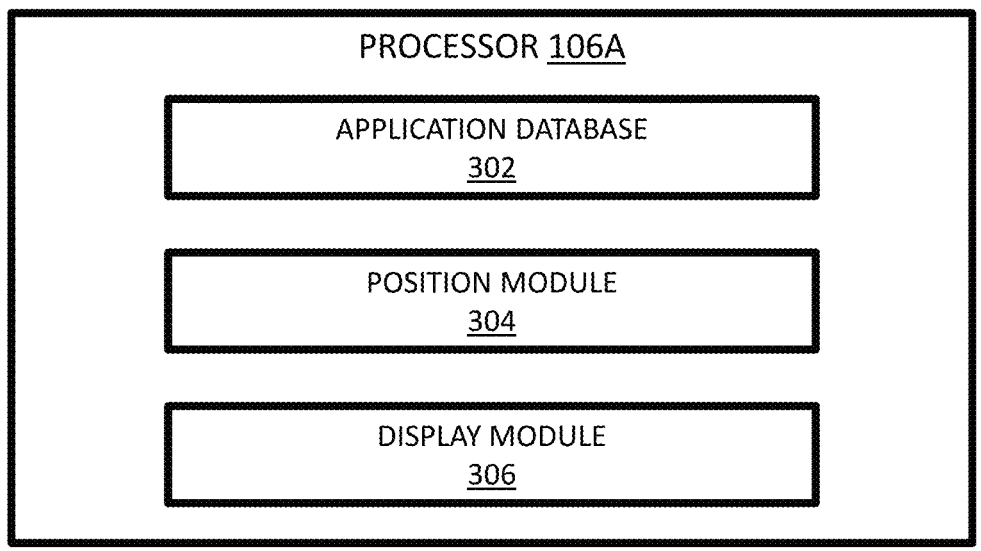
FIGS. 3A and 3B are schematic block diagrams illustrating various embodiments of a processor included in the mobile computing devices of FIGS. 1A and 1B.

With reference to FIG. 3A, FIG. 3A is a schematic block diagram of one embodiment of a processor 106C, which can be one or more embodiments of processor 106A and/or processor 106B. At least in the illustrated embodiment, the processor 106C includes, among other components, an application database 302, a position module 304, and a display module 306 similar to the application database 202, position module 204, and display module 206, respectively, in the memory device 104A discussed with reference to FIG. 2A.

Figure 3B:
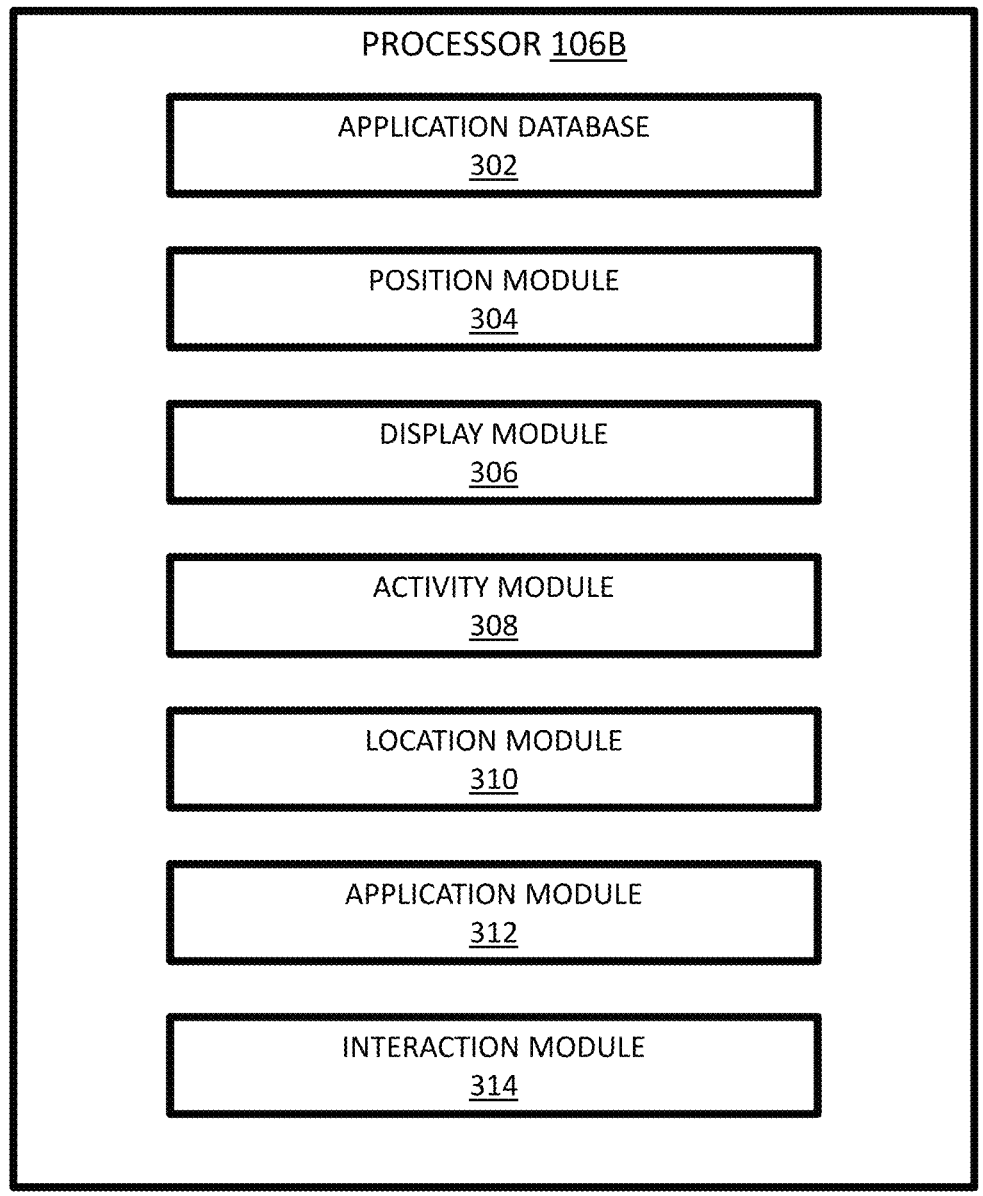

Referring to FIG. 3B, FIG. 3B is a schematic block diagram of another embodiment of a processor 106D, which can be one or more embodiments of processor 106A and/or processor 106B. At least in the illustrated embodiment, the processor 106D includes, among other components, an application database 302, a position module 304, a display module 306, an activity module 308, a location module 310, an application module 312, and an interactive module 314 similar to the application database 202, position module 204, display module 206, activity module 208, location module 210, application module 212, and interactive module 214, respectively, in the memory device 104B discussed with reference to FIG. 2B.

Figure 4:
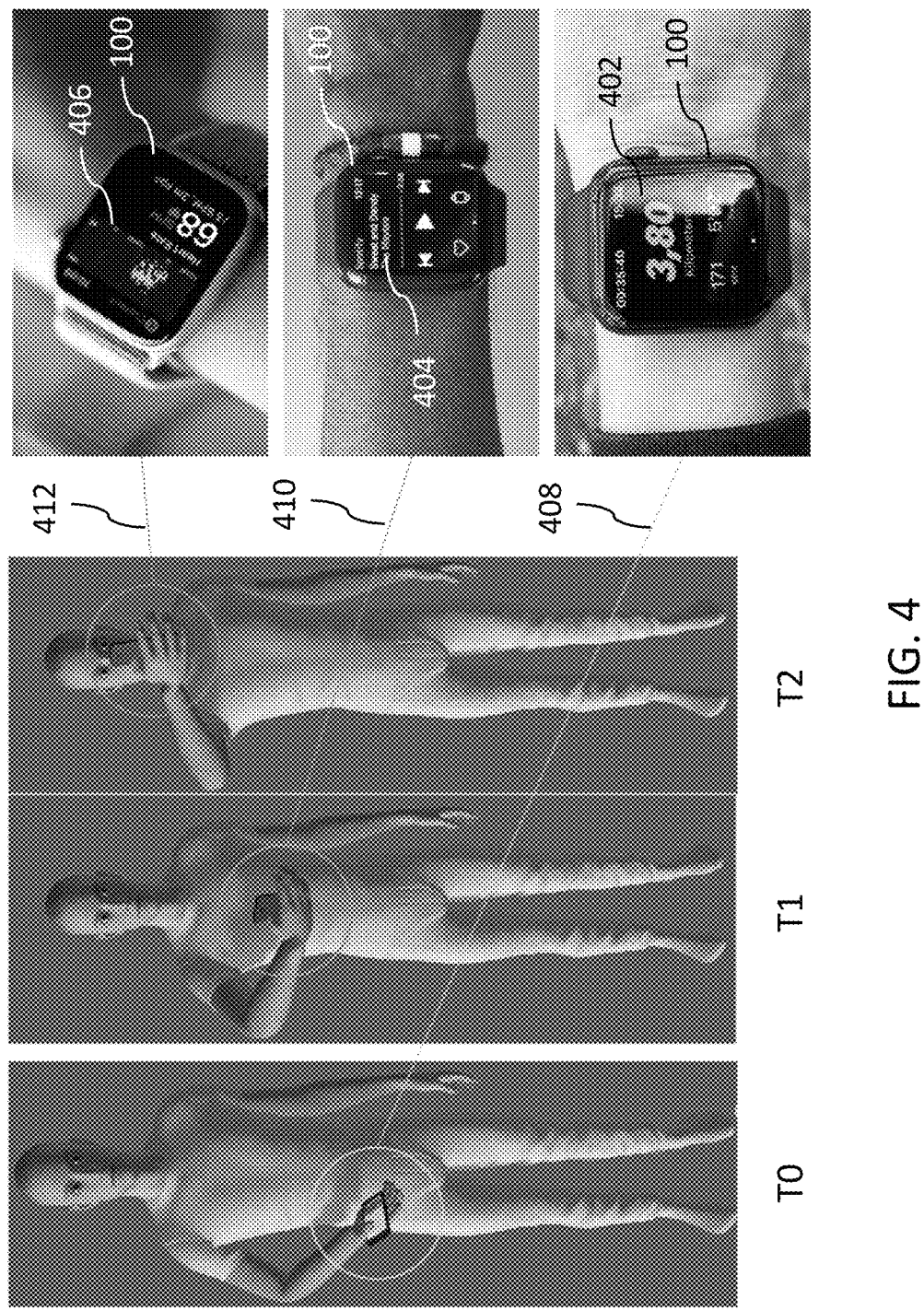
FIG. 4 is schematic diagram illustrating example operations of one embodiment of the mobile computing devices of FIGS. 1A and 1B during an activity.

With reference to FIG. 4, FIG. 4 is a diagram illustrating a non-limiting example of the operations of at least one embodiment of a mobile computing device 100. In the illustrated non-limiting example of FIG. 4, the mobile computing device 100 can include a smartphone or a smartwatch, among other mobile computing devices 100 that are possible and contemplated herein.

Further, this example includes a navigation application 402, a music application 404, and a biometric application 406, among other applications that are possible and contemplated herein. The navigation application 402, music application 404, and biometric application 406 may be selected by the user or automatically selected by the mobile computing device 100, as discussed elsewhere herein.

In addition, the navigation application 402 may be assigned for display on the mobile computing device 100 when the mobile computing device is positioned at a first relative position 408 (e.g., the user's waist), the music application 404 may be assigned for display on the mobile computing device 100 when the mobile computing device is positioned at a second relative position 410 (e.g., the user's chest), and the biometric application 406 may be assigned for display on the mobile computing device 100 when the mobile computing device is positioned at a third relative position 412 (e.g., the user's face), among other possible relative positions and/or assignment of the applications to the various relative positions that are possible and contemplated herein. Furthermore, the navigation application 402 may be assigned to the first relative position 408, the music application 404 may be assigned to the second relative position 410, and the biometric application 406 may be assigned to the third relative position 412 by the user or automatically/automatedly assigned by the mobile computing device 100, as discussed elsewhere herein.

Moreover, the navigation application 402, music application 404, and biometric application 406 may be assigned for display on the mobile computing device 100 based on detection/determination of the user performing this particular activity (e.g., walking) and/or type of activity and/or the user being currently located at this particular geographic location, as discussed elsewhere herein. Furthermore, one or more of the navigation application 402, music application 404, and biometric application 406 may be assigned by the user based on the activity and/or the current geographic location. Additionally, or alternatively, one or more of the navigation application 402, music application 404, and biometric application 406 may be automatically and/or automatedly assigned by the mobile computing device 100 based on the activity and/or the current geographic location, as discussed elsewhere herein.

In FIG. 4, at time T0, the user is positioning the mobile computing device 100 at the first relative position 408 (e.g., the user's waist). In response to detecting that the mobile computing device 100 is positioned at the first relative position 408, the computing device 100 displays the navigation application 402. While at the mobile computing device 100 is positioned at the first relative position 408 and displaying the navigation application 402, the user may provide one or more inputs to the computing device 100 that, when detected (e.g., by the interactive module 214 and/or 314), can display, access, and/or use one or more features of the navigation application 402, as discussed elsewhere herein.

At time T1, the user has moved the mobile computing device 100 to the second relative position 410 (e.g., the user's chest). In response to detecting that the mobile computing device 100 is now positioned at the second relative position 410, the computing device 100 displays the music application 402. While at the mobile computing device 100 is positioned at the second relative position 410 and displaying the music application 404, the user may provide one or more inputs to the computing device 100 that, when detected (e.g., by the interactive module 214 and/or 314), can display, access, and/or use one or more features of the music application 404.

At time T2, the user has moved the mobile computing device 100 to the third relative position 412 (e.g., the user's face). In response to detecting that the mobile computing device 100 is now positioned at the third relative position 412, the computing device 100 displays the biometric application 406. While at the mobile computing device 100 is positioned at the third relative position 412 and displaying the biometric application 406, the user may provide one or more inputs to the computing device 100 that, when detected (e.g., by the interactive module 214 and/or 314), can display, access, and/or use one or more features of the biometric application 406, as discussed elsewhere herein.

Figure 5:
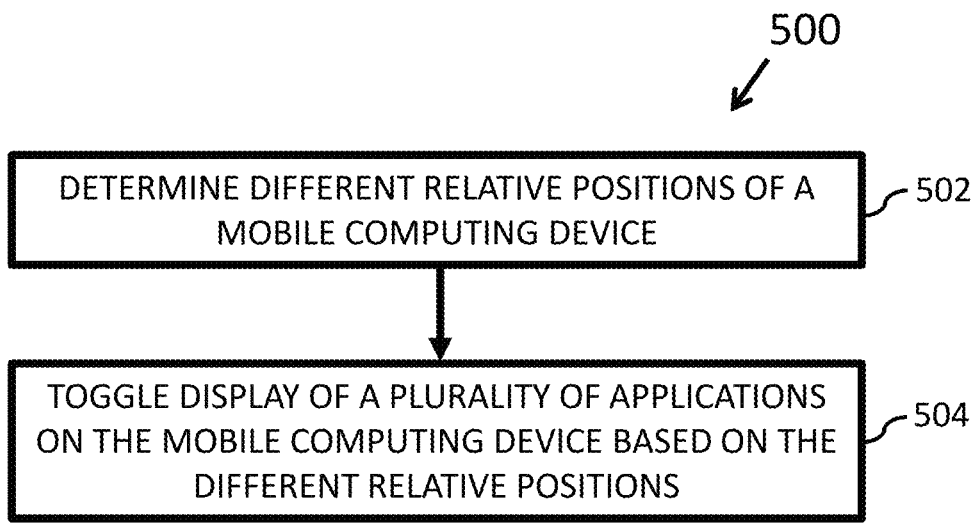
FIG. 5 is a schematic flow chart diagram illustrating one embodiment of a method for display applications on a mobile computing device based on different relative positions of the mobile computing device.

FIG. 5 is a schematic flow chart diagram illustrating one embodiment of a method 500 for displaying applications on a mobile computing device 100 based on different relative positions. At least in the illustrated embodiment, the method 500 begins by a processor (e.g., processor 106) determining different relative positions of a mobile computing device 100 (block 502) while a user is performing an activity.

In some embodiments, the method 500 further includes toggling display of a plurality of applications on the mobile computing device 100 based on the different relative positions of the mobile computing device 100 (block 504) while the user is performing the activity. The user may assign the applications to the different relative locations or the applications may be automatically/automatedly assigned by the processor 106 to the different relative locations, as discussed elsewhere herein.

Figure 6:
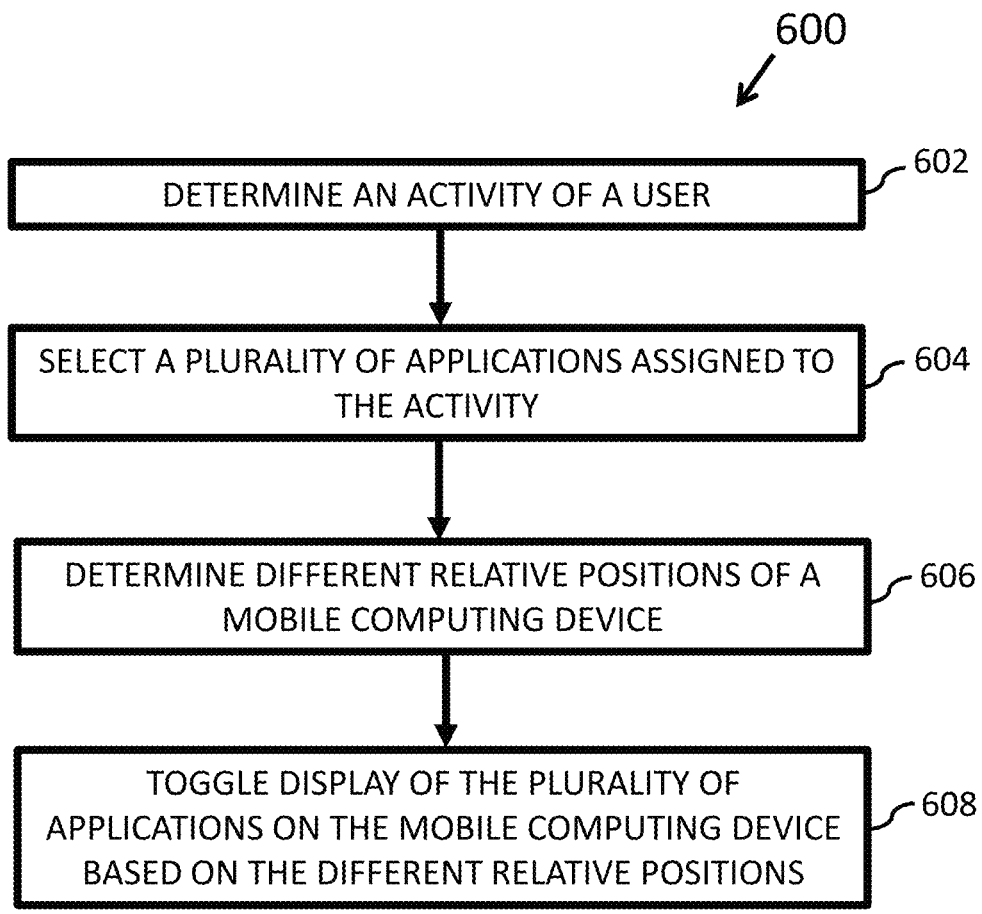
FIG. 6 is a schematic flow chart diagram illustrating another embodiment of a method for display applications on a mobile computing device based on different relative positions of the mobile computing device.

FIG. 6 is a schematic flow chart diagram illustrating another embodiment of a method 600 for displaying applications on a mobile computing device 100 based on different relative positions. At least in the illustrated embodiment, the method 600 begins by a processor (e.g., processor 106) determining an activity that a user is currently performing (block 602) and selecting a plurality of applications assigned to the activity for display on the mobile computing device 100 while the user is performing the activity (block 604).

Here, the processor 106 determines different relative positions of the mobile computing device 100 while the user is performing the activity (block 606). In some embodiments, the processor 106 toggles display of the plurality of applications on the mobile computing device 100 based on the different relative positions of the mobile computing device 100 while the user is performing the activity (block 608).

In method 600, the user may assign the applications to the activity or the applications may be automatically/automatedly assigned by the processor 106 to the activity, as discussed elsewhere herein. In addition, the user may assign the applications to the different relative locations or the applications may be automatically/automatedly assigned by the processor 106 to the different relative locations, as further discussed elsewhere herein.

Figure 7:
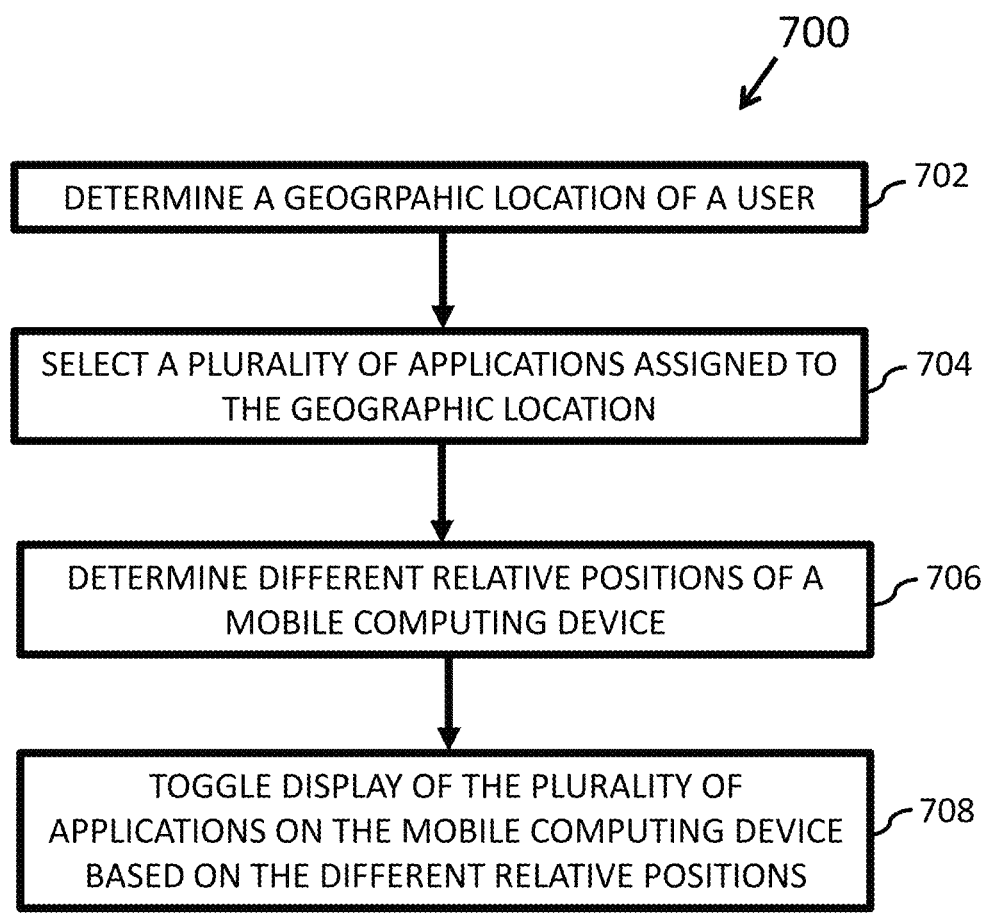
FIG. 7 is a schematic flow chart diagram illustrating yet another embodiment of a method for display applications on a mobile computing device based on different relative positions of the mobile computing device.

FIG. 7 is a schematic flow chart diagram illustrating another embodiment of a method 700 for displaying applications on a mobile computing device 100 based on different relative positions. At least in the illustrated embodiment, the method 700 begins by a processor (e.g., processor 106) determining a geographic location where a user is currently present (block 702) and selecting a plurality of applications assigned to the geographic location for display on the mobile computing device 100 while the user is present at the geographic location (block 704).

Here, the processor 106 determines different relative positions of the mobile computing device 100 while the user is present at the geographic location (block 706). In some embodiments, the processor 106 toggles display of the plurality of applications on the mobile computing device 100 based on the different relative positions of the mobile computing device 100 while the user is present at the geographic location (block 708).

In method 700, the user may assign the applications to the geographic location or the applications may be automatically/automatedly assigned by the processor 106 to the geographic location, as discussed elsewhere herein. In addition, the user may assign the applications to the different relative locations or the applications may be automatically/automatedly assigned by the processor 106 to the different relative locations, as further discussed elsewhere herein.

Figure 8:
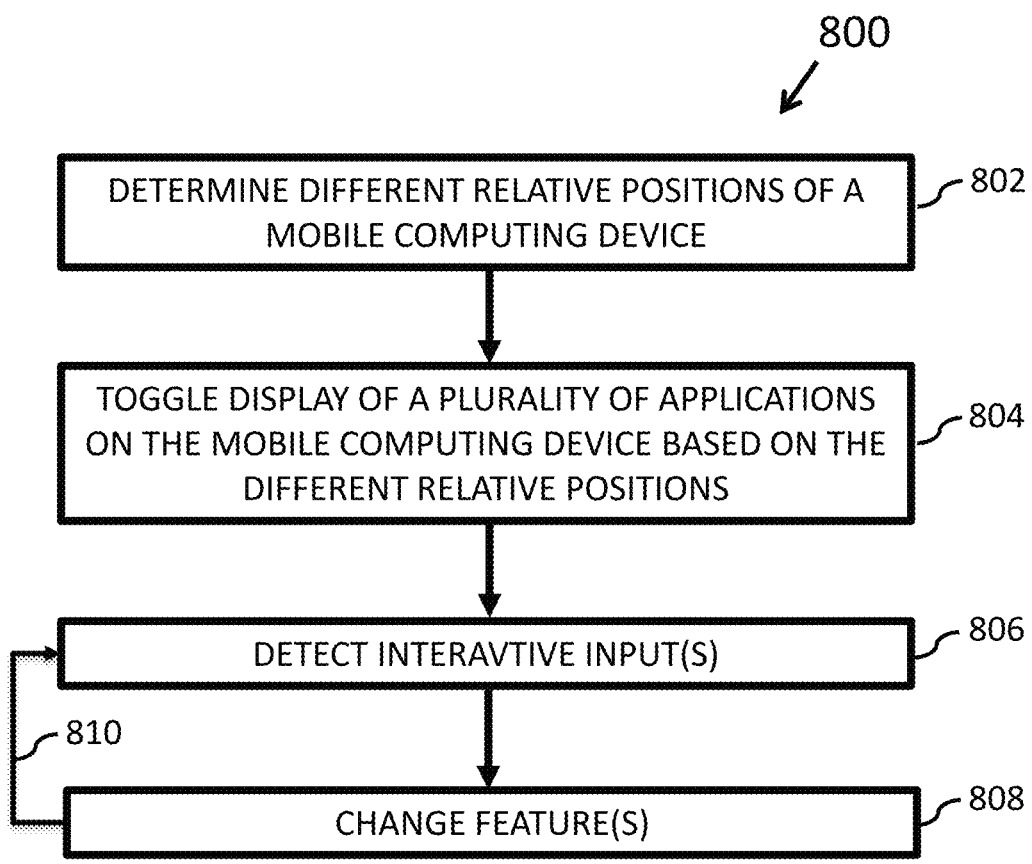
FIG. 8 is a schematic flow chart diagram illustrating still another embodiment of a method for display applications on a mobile computing device based on different relative positions of the mobile computing device.

FIG. 8 is a schematic flow chart diagram illustrating a further embodiment of a method 800 for displaying applications on a mobile computing device 100 based on different relative positions. At least in the illustrated embodiment, the method 800 begins by a processor (e.g., processor 106) determining different relative positions of a mobile computing device 100 while a user is performing an activity (block 802).

In some embodiments, the method 800 further includes toggling display of a plurality of applications on the mobile computing device 100 based on the different relative positions of the mobile computing device 100 while the user is performing the activity (block 804). Further, the processor 106 can detect one or more user inputs (e.g., interactive inputs) to the mobile computing device 100 while an application is being displayed on the mobile computing device 100 (block 806).

In response to detecting the input(s), the processor changes one or more features of the currently displayed application (block 808). Blocks 806 and 808 can be repeated as further inputs are detected (return 810).

In method 800, the user may assign the applications to the different relative locations or the applications may be automatically/automatedly assigned by the processor 106 to the different relative locations, as discussed elsewhere herein. Further, the user may assign the input(s) to the application(s) or the input(s) may be automatically/automatedly assigned by the processor 106 to the application(s), as discussed elsewhere herein.

Figure 9:
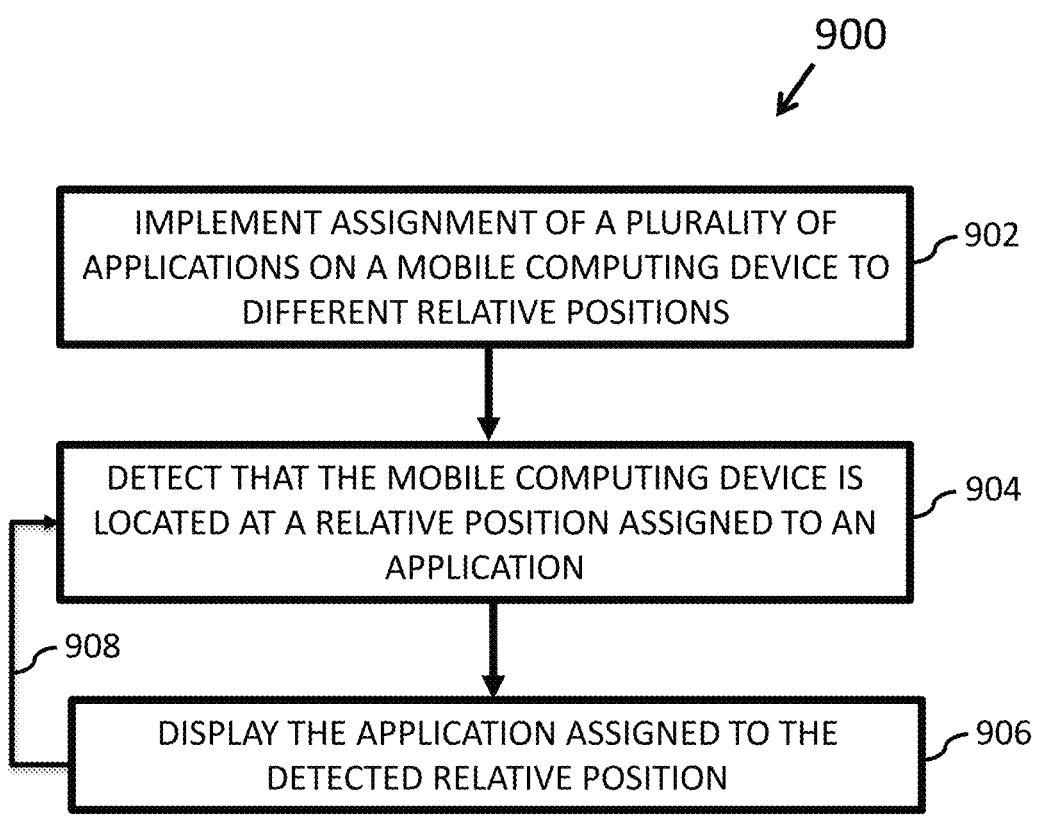
FIG. 9 is a schematic flow chart diagram illustrating a further embodiment of a method for display applications on a mobile computing device based on different relative positions of the mobile computing device.

FIG. 9 is a schematic flow chart diagram illustrating another embodiment of a method 900 for displaying applications on a mobile computing device 100 based on different relative positions. At least in the illustrated embodiment, the method 900 begins by a processor (e.g., processor 106) implementing an assignment of a plurality of applications to different relative positions (block 902). As discussed elsewhere herein, the user may assign the applications to the different relative positions or the applications may be automatically/automatedly assigned by the processor 106 to the different relative positions.

Next, the processor 106 detects that the mobile computing device 100 is located/positioned at a relative position (block 904). In response to detecting that the mobile computing device 100 is located/positioned at a relative position assigned to a particular application, the processor 106 displays on the mobile computing device 100 the application corresponding to and/or associated with the relative position (block 906). The processor 106 can repeat blocks 904 and 906 responsive to the processor 106 detecting that the mobile computing device 100 has changed moved (return 908).

As discussed herein, the various embodiments disclose apparatus, methods, and computer program products. Specifically, the disclosed embodiments can display applications on a mobile computing device 100 based on different relative positions.

An apparatus, in one embodiment, includes a processor and a memory that stores code executable by the processor. In certain embodiments, the code is executable by the processor to determine different relative positions of a mobile computing device while a user is performing an activity and toggle display of a plurality of applications on the mobile computing device based on the different relative positions of the mobile computing device while the user is performing the activity. In additional embodiments, the code further causes the processor to determine the activity that the user is currently performing and select the plurality of applications for display on the mobile computing device while the user is performing the activity based on the determined activity.

In some embodiments, determining the different relative positions of the mobile computing device comprises determining that the mobile computing device is located at a first relative position and toggling display of the plurality of applications on the mobile computing device comprises displaying on the mobile computing device a first application of the plurality of applications assigned to the first relative position. In additional embodiments, determining the different relative positions of the mobile computing device comprises determining that the mobile computing device is located at a second relative position and toggling display of the plurality of applications on the mobile computing device based on the different relative positions comprises displaying on the mobile computing device a second application of the plurality of applications assigned to the second relative position.

In certain embodiments, determining the different relative positions of the mobile computing device comprises determining that the mobile computing device is located at a first relative position and toggling display of the plurality of applications on the mobile computing device comprises displaying on the mobile computing device a first application of the plurality of applications assigned to the first relative position. Here, the processor is further configured to determine a first user interaction with the mobile computing device while the mobile computing device is located at the first relative position and perform a first feature of the first application responsive to the determined first user interaction.

In additional embodiments, the processor is further configured to determine a second user interaction with the mobile computing device while the mobile computing device is located at the first relative position and perform a second feature of the first application responsive to the determined second user interaction. In some embodiments, determining the different relative positions of the mobile computing device comprises determining that the mobile computing device is located at a second relative position, toggling display of the plurality of applications on the mobile computing device comprises displaying on the mobile computing device a second application of the plurality of applications assigned to the second relative position, and the processor is further configured to determine a third user interaction with the mobile computing device while the mobile computing device is located at the second relative position and perform a third feature of the second application responsive to the determined third user interaction. In further embodiments, the processor is configured to determine a fourth user interaction with the mobile computing device while the mobile computing device is located at the second relative position and perform a fourth feature of the second application responsive to the determined fourth user interaction.

In additional embodiments, the plurality of applications are assigned to the different relative positions by the user or the plurality of applications are automatically assigned to the different relative positions in response to the processor identifying a historical usage of the plurality of applications by the user while performing the activity. In some additional or alternative embodiments, the plurality of applications are assigned to the activity by the user or the plurality of applications are automatically assigned to the activity in response to the processor identifying a historical usage of the plurality of applications by the user while performing the activity.

One embodiment of a method that can display applications on a mobile computing device based on different relative positions includes determining, by a processor, different relative positions of a mobile computing device user while a user is performing an activity. In some embodiments, the method further includes toggling display of a plurality of applications on the mobile computing device based on the different relative positions of the mobile computing device while the user is performing the activity. In additional embodiments, the method further comprises determining the activity that the user is currently performing and selecting the plurality of applications for display on the mobile computing device while the user is performing the activity based on the determined activity.

In some embodiments, determining the different relative positions of the mobile computing device comprises determining that the mobile computing device is located at a first relative position and toggling display of the plurality of applications on the mobile computing device comprises displaying on the mobile computing device a first application of the plurality of applications assigned to the first relative position. In additional embodiments, determining the different relative positions of the mobile computing device comprises determining that the mobile computing device is located at a second relative position and toggling display of the plurality of applications on the mobile computing device based on the different relative positions comprises displaying on the mobile computing device a second application of the plurality of applications assigned to the second relative position.

In certain embodiments, determining the different relative positions of the mobile computing device comprises determining that the mobile computing device is located at a first relative position and toggling display of the plurality of applications on the mobile computing device comprises displaying on the mobile computing device a first application of the plurality of applications assigned to the first relative position. Here, the method further comprises determining a first user interaction with the mobile computing device while the mobile computing device is located at the first relative position and performing a first feature of the first application responsive to the determined first user interaction.

In additional embodiments, the method further comprises determining a second user interaction with the mobile computing device while the mobile computing device is located at the first relative position and performing a second feature of the first application responsive to the determined second user interaction. In some embodiments, determining the different relative positions of the mobile computing device comprises determining that the mobile computing device is located at a second relative position, toggling display of the plurality of applications on the mobile computing device comprises displaying on the mobile computing device a second application of the plurality of applications assigned to the second relative position, and the method further comprises determining a third user interaction with the mobile computing device while the mobile computing device is located at the second relative position and performing a third feature of the second application responsive to the determined third user interaction. In further embodiments, the method further comprises determining a fourth user interaction with the mobile computing device while the mobile computing device is located at the second relative position and performing a fourth feature of the second application responsive to the determined fourth user interaction.

In additional embodiments, the method further comprises receiving, from the user, assignment of the plurality of applications to the different relative positions or automatically assigning the plurality of applications to the different relative positions responsive to the processor identifying a historical usage of the plurality of applications by the user while performing the activity. In some additional or alternative embodiments, the method further comprises receiving, from the user, assignment of the plurality of applications to the activity or automatically assigning the plurality of applications to the activity responsive to the processor identifying a historical usage of the plurality of applications by the user while performing the activity.

A computer program product that can display applications on a mobile computing device based on different relative positions, in one embodiment, includes a computer-readable storage medium including program instructions embodied therewith. In certain embodiments, the program instructions are executable by a processor to cause the processor to determine different relative positions of a mobile computing device while the user is performing an activity and toggle display of a plurality of applications on the mobile computing device based on the different relative positions of the mobile computing device while the user is performing the activity. In additional embodiments, the program instructions further cause the processor to determine the activity that the user is currently performing and select the plurality of applications for display on the mobile computing device while the user is performing the activity based on the determined activity.

In some embodiments, determining the different relative positions of the mobile computing device comprises determining that the mobile computing device is located at a first relative position and toggling display of the plurality of applications on the mobile computing device comprises displaying on the mobile computing device a first application of the plurality of applications assigned to the first relative position. In additional embodiments, determining the different relative positions of the mobile computing device comprises determining that the mobile computing device is located at a second relative position and toggling display of the plurality of applications on the mobile computing device based on the different relative positions comprises displaying on the mobile computing device a second application of the plurality of applications assigned to the second relative position.

In certain embodiments, determining the different relative positions of the mobile computing device comprises determining that the mobile computing device is located at a first relative position and toggling display of the plurality of applications on the mobile computing device comprises displaying on the mobile computing device a first application of the plurality of applications assigned to the first relative position. Here, the program instructions further cause the processor to determine a first user interaction with the mobile computing device while the mobile computing device is located at the first relative position and perform a first feature of the first application responsive to the determined first user interaction.

In additional embodiments, the program instructions further cause the processor to determine a second user interaction with the mobile computing device while the mobile computing device is located at the first relative position and perform a second feature of the first application responsive to the determined second user interaction. In some embodiments, determining the different relative positions of the mobile computing device comprises determining that the mobile computing device is located at a second relative position, toggling display of the plurality of applications on the mobile computing device comprises displaying on the mobile computing device a second application of the plurality of applications assigned to the second relative position, and the program instructions further cause the processor to determine a third user interaction with the mobile computing device while the mobile computing device is located at the second relative position and perform a third feature of the second application responsive to the determined third user interaction. In further embodiments, the program instructions cause the processor to determine a fourth user interaction with the mobile computing device while the mobile computing device is located at the second relative position and perform a fourth feature of the second application responsive to the determined fourth user interaction.

In additional embodiments, the plurality of applications are assigned to the different relative positions by the user or the plurality of applications are automatically assigned to the different relative positions in response to the processor identifying a historical usage of the plurality of applications by the user while performing the activity. In some additional or alternative embodiments, the plurality of applications are assigned to the activity by the user or the plurality of applications are automatically assigned to the activity in response to the processor identifying a historical usage of the plurality of applications by the user while performing the activity.

Embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computer program product comprising a non-transitory computer-readable storage device including code embodied therewith, the code executable by a processor to cause the processor to:
   determine different relative positions of a mobile computing device while a user is performing an activity; and
   toggle display of a plurality of applications on the mobile computing device based on the different relative positions of the mobile computing device while the user is performing the activity,
   wherein:
      determining the different relative positions of the mobile computing device comprises determining that the mobile computing device is located at a first relative position, and
      toggling display of the plurality of applications on the mobile computing device comprises displaying on the mobile computing device a first application of the plurality of applications assigned to the first relative position.

2. An apparatus, comprising:
   a processor; and
   a memory configured to store code executable by the processor to:
      determine different relative positions of a mobile computing device while a user is performing an activity, and
      toggle display of a plurality of applications on the mobile computing device based on the different relative positions of the mobile computing device while the user is performing the activity,
      wherein toggling display of the plurality of applications on the mobile computing device comprises displaying on the mobile computing device a first application of the plurality of applications assigned to a first relative position.

3. The apparatus of claim 2, wherein the code further causes the processor to:
   determine the activity that the user is currently performing; and
   select the plurality of applications for display on the mobile computing device while the user is performing the activity based on the determined activity.

4. The apparatus of claim 3, wherein:
   the processor is further configured to:
      determine a first user interaction with the mobile computing device while the mobile computing device is located at the first relative position, and
      perform a first feature of the first application responsive to the determined first user interaction.

5. The apparatus of claim 4, wherein the processor is further configured to:
   determine a second user interaction with the mobile computing device while the mobile computing device is located at the first relative position; and
   perform a second feature of the first application responsive to the determined second user interaction.

6. The apparatus of claim 5, wherein:
   determining the different relative positions of the mobile computing device comprises determining that the mobile computing device is located at a second relative position;
   toggling display of the plurality of applications on the mobile computing device comprises displaying on the mobile computing device a second application of the plurality of applications assigned to the second relative position; and
   the processor is further configured to:
      determine a third user interaction with the mobile computing device while the mobile computing device is located at the second relative position, and
      perform a third feature of the second application responsive to the determined third user interaction.

7. The apparatus of claim 6, wherein the processor is further configured to:
   determine a fourth user interaction with the mobile computing device while the mobile computing device is located at the second relative position; and
   perform a fourth feature of the second application responsive to the determined fourth user interaction.

8. The apparatus of claim 2, wherein:
determining the different relative positions of the mobile computing device comprises determining that the mobile computing device is located at the first relative position.

9. The apparatus of claim 8, wherein:
determining the different relative positions of the mobile computing device comprises determining that the mobile computing device is located at a second relative position; and
toggling display of the plurality of applications on the mobile computing device based on the different relative positions comprises displaying on the mobile computing device a second application of the plurality of applications assigned to the second relative position.

10. The apparatus of claim 1, wherein one of:
the plurality of applications are assigned to the different relative positions by the user; and
the plurality of applications are automatically assigned to the different relative positions in response to the processor identifying a historical usage of the plurality of applications by the user while performing the activity.

11. The apparatus of claim 10, wherein one of:
the plurality of applications are assigned to the activity by the user; and
the plurality of applications are automatically assigned to the activity in response to the processor identifying a historical usage of the plurality of applications by the user while performing the activity.

12. A method, comprising:
determining, by a processor, different relative positions of a mobile computing device while a user is performing an activity; and
toggling display of a plurality of applications on the mobile computing device based on the different relative positions of the mobile computing device while the user is performing the activity,
wherein toggling display of the plurality of applications on the mobile computing device comprises displaying on the mobile computing device a first application of the plurality of applications assigned to a first relative position.

13. The method of claim 12, further comprising:
determining the activity that the user is currently performing; and
selecting the plurality of applications for display on the mobile computing device while the user is performing the activity based on the determined activity.

14. The method of claim 13, wherein:
the method further comprises:
determining a first user interaction with the mobile computing device while the mobile computing device is located at the first relative position, and
performing a first feature of the first application responsive to the determined first user interaction.

15. The method of claim 14, further comprising:
determining a second user interaction with the mobile computing device while the mobile computing device is located at the first relative position; and
performing a second feature of the first application responsive to the determined second user interaction.

16. The method of claim 15, wherein:
determining the different relative positions of the mobile computing device comprises determining that the mobile computing device is located at a second relative position;
toggling display of the plurality of applications on the mobile computing device comprises displaying on the mobile computing device a second application of the plurality of applications assigned to the second relative position; and
the method further comprises:
determining a third user interaction with the mobile computing device while the mobile computing device is located at the second relative position, and
performing a third feature of the second application responsive to the determined third user interaction.

17. The method of claim 16, further comprising:
determining a fourth user interaction with the mobile computing device while the mobile computing device is located at the second relative position; and
performing a fourth feature of the second application responsive to the determined fourth user interaction.

18. The method of claim 12, wherein:
determining the different relative positions of the mobile computing device comprises determining that the mobile computing device is located at the first relative position.

19. The method of claim 18, wherein:
determining the different relative positions of the mobile computing device comprises determining that the mobile computing device is located at a second relative position; and
toggling display of the plurality of applications on the mobile computing device based on the different relative positions comprises displaying on the mobile computing device a second application of the plurality of applications assigned to the second relative position.

20. The method of claim 12, wherein:
the method further comprises one of:
receiving, from the user, assignment of the plurality of applications to the different relative positions, and
automatically assigning the plurality of applications to the different relative positions responsive to the processor identifying a historical usage of the plurality of applications by the user while performing the activity; and
the method further comprises one of:
receiving, from the user, assignment of the plurality of applications to the activity, and
automatically assigning the plurality of applications to the activity responsive to the processor identifying a historical usage of the plurality of applications by the user while performing the activity.

\* \* \* \* \*